US010849608B2

(12) United States Patent
Arshava

(10) Patent No.: US 10,849,608 B2
(45) Date of Patent: Dec. 1, 2020

(54) TRANSHIATAL MEDIASTINAL RETRACTOR

(71) Applicant: University of Iowa Research Foundation, Iowa City, IA (US)

(72) Inventor: Evgeny Arshava, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 141 days.

(21) Appl. No.: 16/154,388

(22) Filed: Oct. 8, 2018

(65) Prior Publication Data
US 2019/0105026 A1 Apr. 11, 2019

Related U.S. Application Data

(60) Provisional application No. 62/569,653, filed on Oct. 9, 2017, provisional application No. 62/691,789, filed on Jun. 29, 2018.

(51) Int. Cl.
| | | |
|---|---|---|
| A61B 17/02 | (2006.01) | |
| A61B 90/30 | (2016.01) | |
| A61B 17/00 | (2006.01) | |
| A61B 90/00 | (2016.01) | |
| A61B 1/267 | (2006.01) | |

(52) U.S. Cl.
CPC ............ *A61B 17/02* (2013.01); *A61B 1/267* (2013.01); *A61B 90/30* (2016.02); *A61B 90/361* (2016.02); *A61B 2017/00296* (2013.01); *A61B 2090/306* (2016.02); *A61B 2090/309* (2016.02)

(58) Field of Classification Search
CPC ......... A61B 17/02; A61B 1/237; A61B 90/30; A61B 1/267
See application file for complete search history.

(56) References Cited

U.S. PATENT DOCUMENTS

| | | | | |
|---|---|---|---|---|
| 2,863,444 A | * | 12/1958 | Winsten ................ | A61B 17/02 600/214 |
| 4,616,633 A | * | 10/1986 | Vargas Garcia ....... | A61B 17/02 600/206 |
| 4,934,352 A | * | 6/1990 | Sullivan, Jr. .......... | A61B 17/02 600/213 |
| 5,514,076 A | | 5/1996 | Ley | |
| 5,514,077 A | * | 5/1996 | Rabban ................. | A61B 17/02 16/430 |
| 6,416,465 B2 | | 7/2002 | Brau | |
| D511,383 S | * | 11/2005 | Stanger ................ | D24/135 |
| D523,142 S | * | 6/2006 | Stalcup ................ | D24/135 |

(Continued)

OTHER PUBLICATIONS

Orringer, Mark B., "Transhiatal Esophagectomy without Thoracotomy", Operative Techniques in Thoracic and Cardiovascular Surgery, vol. 10, Issue 1, pp. 63-83, 2005.

(Continued)

*Primary Examiner* — Christian A Sevilla
(74) *Attorney, Agent, or Firm* — McKee, Voorhees & Sease, PLC

(57) ABSTRACT

A hand-held tool is provided for retraction of internal organs during transhiatal mediastinal surgery. The tool includes a handle and a blade extending forwardly from the handle. The blade has an acute end extending rearwardly and then curves forwardly and upwardly to form an open mouth for receiving the organ.

25 Claims, 7 Drawing Sheets

(56) References Cited

U.S. PATENT DOCUMENTS

D724,207 S    3/2015   Sutherland et al.

OTHER PUBLICATIONS

"Deaver Retractor #5", http://www.sklarcorp.com/deaver-retractor-707.htm, Sklar Surgical Instruments, access by Applicant Oct. 4, 2018.
"Willauer-Deaver Retractor", http://www.teleflexsurgicalcatalog.com/pilling/product/341720-willauer-deaver-retractor, Teleflex Incorporated—Pilling Surgical Instruments Catalog, accessed by Applicant Oct. 4, 2018.

* cited by examiner

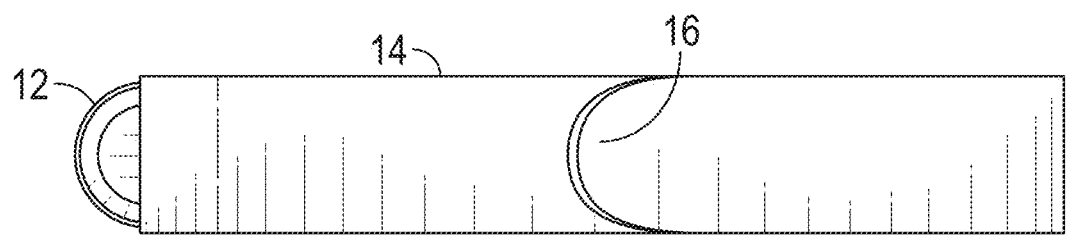
FIG. 5
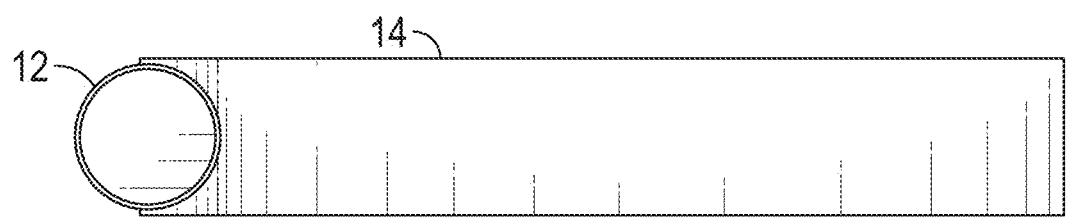
FIG. 6
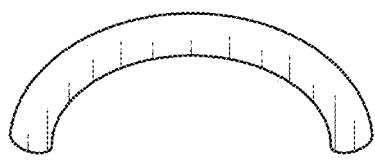 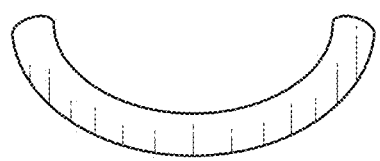
FIG. 7         FIG. 8

TRANSHIATAL MEDIASTINAL RETRACTOR

CROSS-REFERENCE TO RELATED APPLICATIONS

This application claims priority to Provisional Application U.S. Ser. No. 62/569,653, filed on Oct. 9, 2017 and Provisional Application U.S. Ser. No. 62/691,789 filed on Jun. 29, 2018, both of which are herein incorporated by reference in their entirety.

BACKGROUND OF THE INVENTION

Transhiatal esophagectomy surgical procedures began in the mid-1970's as an alternative to transthoracic esophagectomy. Hand held retractors are used to retract tissues and organs during the transhiatal esophagectomy to provide visual access within the thoracic cavity. A Deaver retractor, which is a multi-purpose abdominal retractor, is most commonly used for this purpose. Conventional tools are limited in the ability to move and lift organs and tissues due to the shape of the tools. Therefore, there is a need for an improved retractor that provides enhanced exposure of the posterior mediastinum during transhiatal esophagostomy.

Accordingly, a primary objective of the present invention is the provision of a surgical instrument or tool for transhiatal mediastinal retraction whose shape and structural characteristics provide advantages and improvements over existing surgical retractors.

Another objective of the present invention is the provision of an improved retractor for use by general thoracic and foregut surgeons performing open transhiatal esophagostomies and other operations through the diaphragmatic hiatus.

Another objective of the present invention is the provision of a retractor instrument for use in esophagus, thorax, abdomen, and stomach surgery.

Yet another objective of the present invention is the provision of a surgical retractor tool having a stiff blade with an acute retraction angle.

Still another objective of the present invention is the provision of a surgical retractor having a C-shaped blade for improved visualization and stability.

A further objective of the present invention is a provision a surgical retractor having a light mounted thereon.

An additional objective of the present invention is a provision of a surgical retractor having a video camera to facilitate visualization of the posterior mediastinum through the diaphragmatic hiatus with transmission of video signal onto a monitor.

Another objection of the present invention is a provision of a surgical retractor instrument having a blade to provide enhanced exposure of the posterior mediastinum.

Still another objective of the present invention is a provision of a surgical retractor which is economical to manufacture, and durable and safe in use.

SUMMARY OF THE INVENTION

Disclosed herein are surgical tools that are useful for transhiatal mediastinal retraction during surgical procedures. In some embodiments, the surgical tools are retractors that include a handle, and a blade extending forwardly from the handle and having an acute bend extending rearwardly and then curving forwardly and upwardly to an end defining an open mouth in a forward direction. In some embodiments, the blade of the surgical tool is non-flexible and can be flat, and the cross-section of the blade can be concave or convex.

In some embodiments, the surgical tools have an acute bend ranging from 10-80°. The acute bend is depicted in FIGS. 4A, 4B, 4C, and 4D. In some embodiments the surgical tools have a bend of approximately 45°. In alternative embodiments, the surgical tools can have a light on the blade for illuminating the thoracic cavity. In these embodiments, the light can be mounted 1 to 6 inches from the end of the blade (FIGS. 13-15). Moreover, the light source can be an LED electrically connected to a power source or a fiber optic cable connected to a light source. In these embodiments, the electrical connection can be a flexible, conductive wire positioned along the exterior side of the blade. Similarly, in embodiments utilizing fiber optic lighting, the fiber can be positioned along the exterior side of the blade.

In alternative embodiments, the surgical tools can have a camera mounted near the end of the blade, for example, within 7 inches from the tip of the blade (FIG. 14). In these embodiments, the camera can be electrically connected (hard wired or wirelessly) to a monitor allowing for the visualization of the thoracic cavity. Similarly, in some embodiments, both the light and camera can be mounted on the blade.

In some embodiments, surgical tools for transhiatal mediastinal retraction include a fastener located on the blade extending forwardly from the handle. One of ordinary skill in the art will appreciate that the fastener can comprise any mechanical mechanism or adapter that will allow the adapter to support with the retractor. One of the ordinary skill in the art will appreciate that the adapter can be designed to include any appropriate mechanical means of attaching the surgical tool to a securing arm or bar of the available table-mounted retractor system (FIG. 15). For example, the adapter can be a rod, bar, paddle, or similar structure. Moreover, the adapter can be attached to a securing arm or bar of the available table-mounted retractor system. One of the ordinary skill in the art will appreciate that the securing arm can be designed to include any appropriate mechanical means to allow the surgical tools for transhiatal mediastinal retraction to be mounted to an operation table. The securing arm can be a pole with clamp, or other mechanical means of securing the adapter in a fixed position.

BRIEF DESCRIPTION OF THE DRAWINGS

FIG. 5 is a front-end elevation view of the retractor shown in FIG. 1.

FIG. 6 is a rear end elevation view of the retractor shown in FIG. 1.

FIG. 7 is an end view of an alternative retractor blade having a convex cross section.

FIG. 8 is an end view of an alternative retractor blade having a concave cross section.

DETAILED DESCRIPTION OF THE INVENTION

Figure 1:
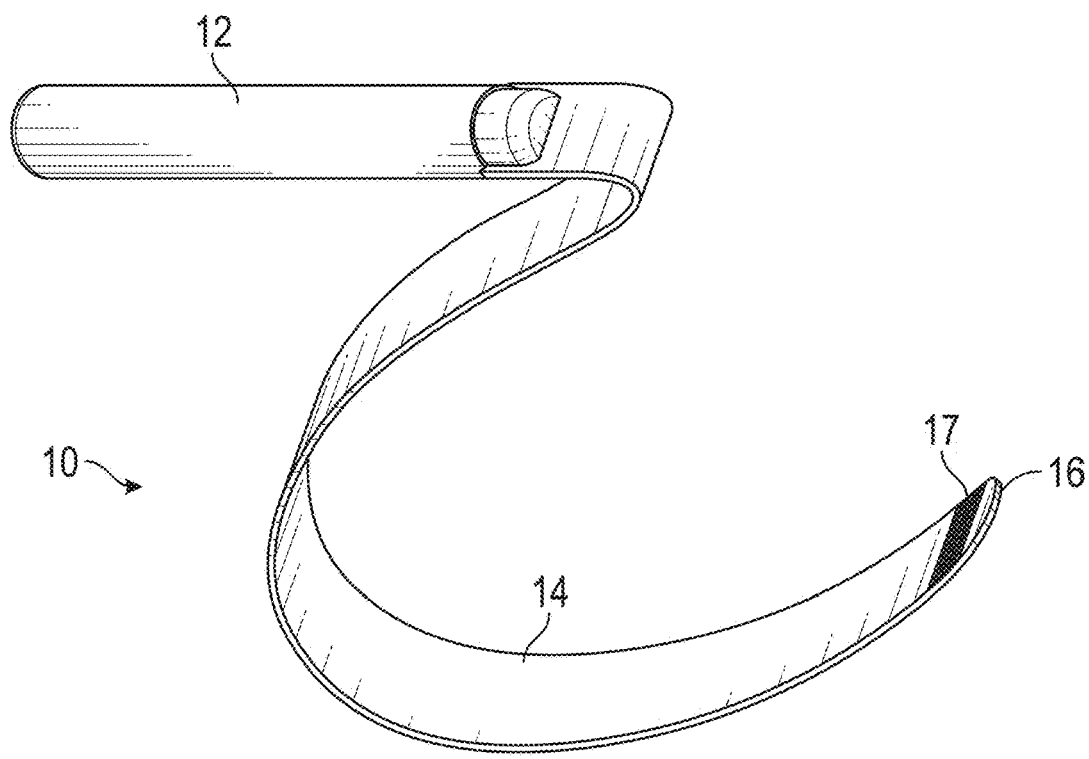
FIG. 1 is a perspective view of a first embodiment for the transhiatal mediastinal retractor, according to the present invention.
Figure 2:
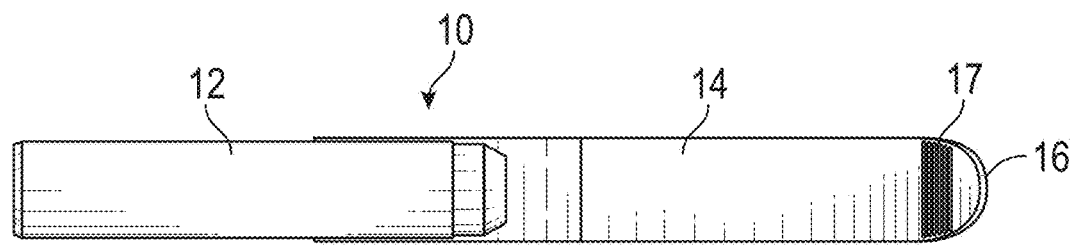
FIG. 2 is a top plan view of the retractor shown in FIG. 1.
Figure 3:
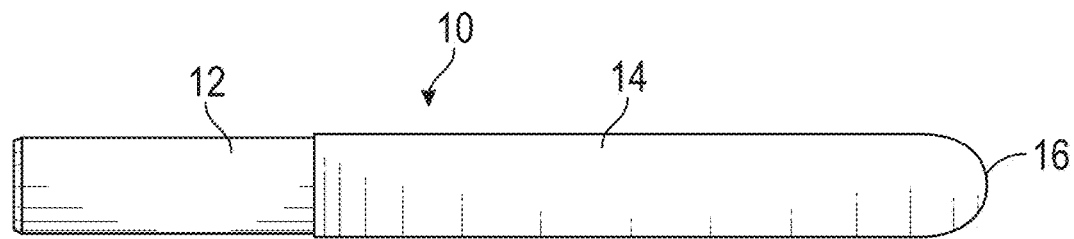
FIG. 3 is a bottom plan view of the retractor shown in FIG. 1.
Figure 4A:
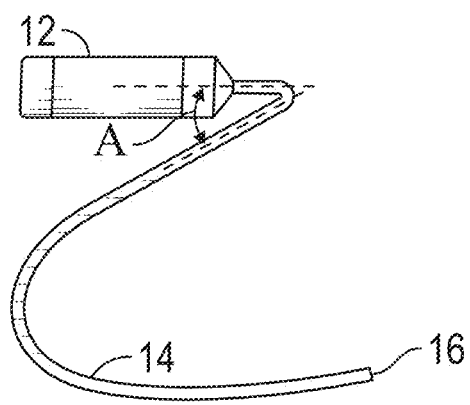
FIGS. 4A, 4B, 4C, and 4D show alternative configurations for the retractor tool, according to the present invention.
Figure 4B:
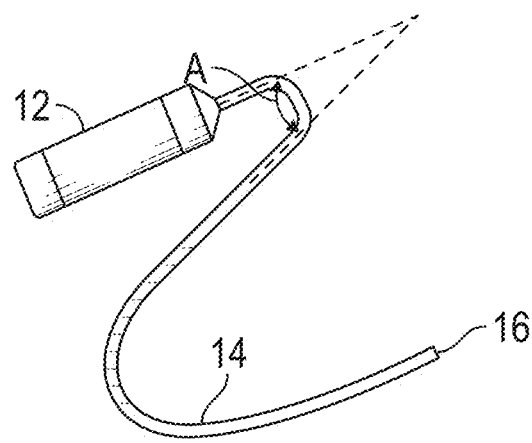
Figure 4C:
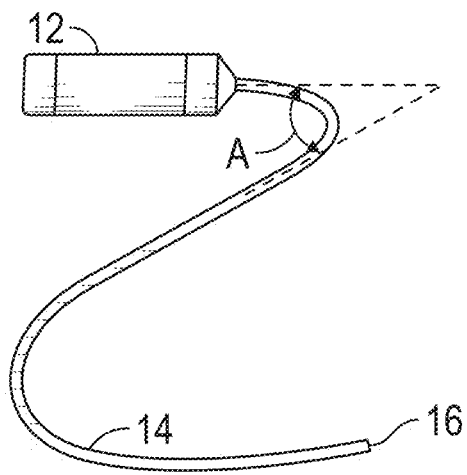
Figure 4D:
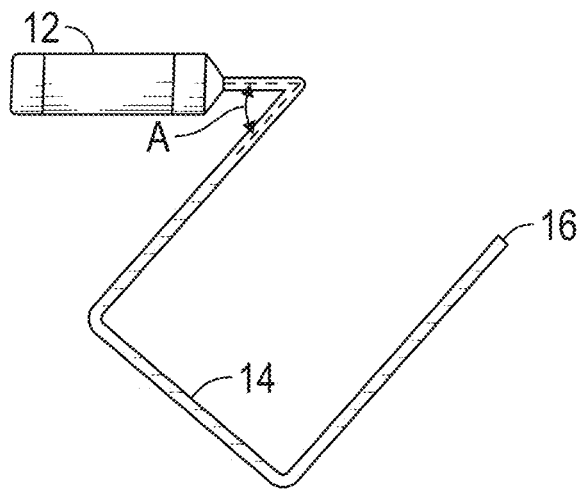

A first embodiment of the transhiatal mediastinal retractor of the present invention is shown in FIGS. 1-6 and generally designated by the reference numeral 10. The retractor 10 comprises a handle 12 and a blade 14.

Figure 9:
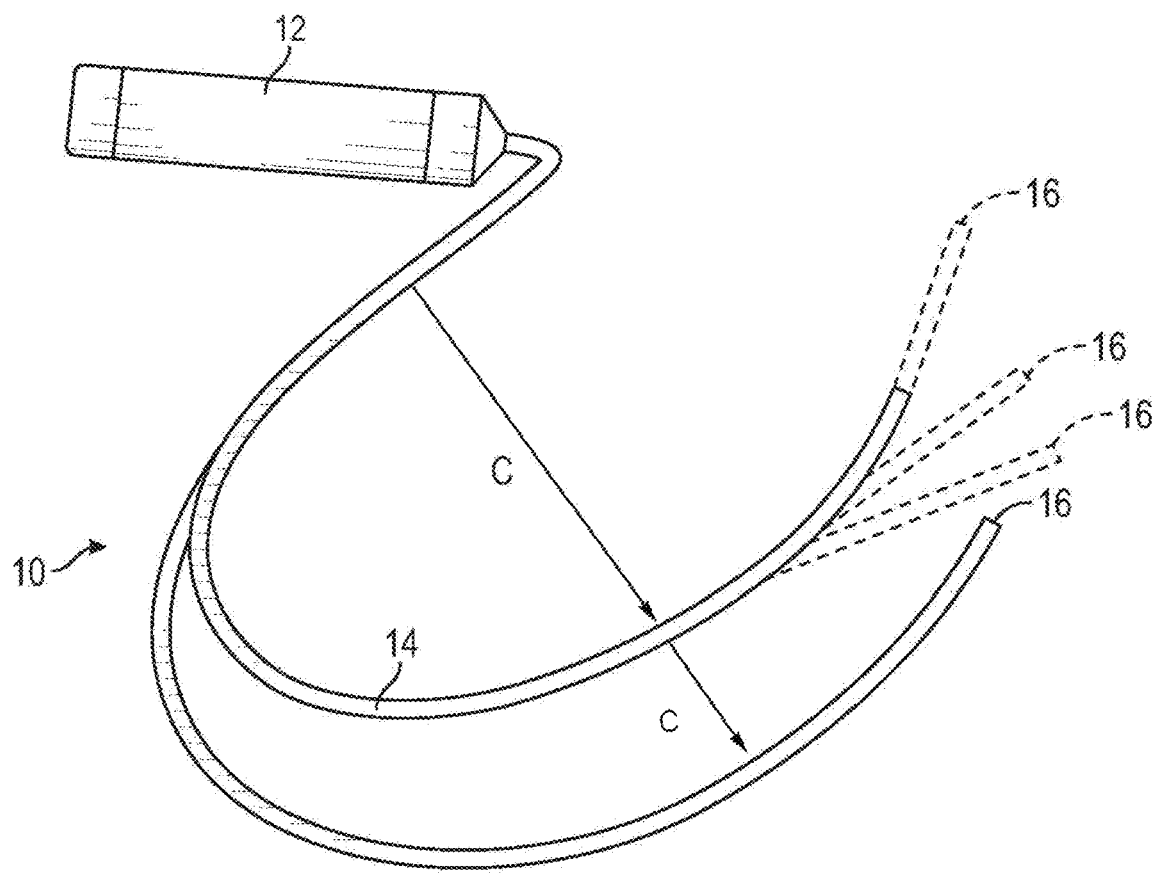
FIG. 9 compares Applicant's standard size retractor with a larger bariatric retractor and demonstrating possible variability of the blade tip angle and width of the blade depth "C."
Figure 10:
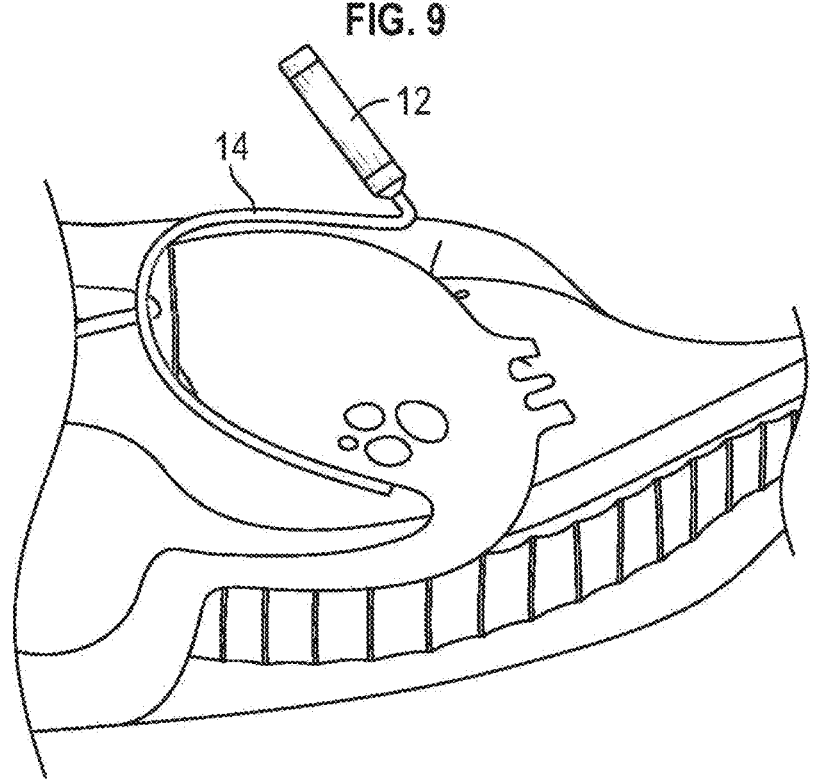
FIG. 10 shows Applicant's retractor in use.

The handle 12 may take various shapes without departing from the present invention. The blade 14 extends forwardly from the handle 12, and then has a reverse or acute angle bend and extends in a C-shape, as best seen in FIGS. 4A-4D. The C-shaped blade 14 defines an open mouth for receiving a tissue or organ to be retracted. The mouth is generally open forwardly opposite the handle 12, such that the retractor 10 can be easily positioned around the tissue or organ so as to move and/or lift the tissue or organ, and thereby allow enhanced visual access for the surgeon. The width of the mouth "C" may vary depending on the angle and length of the blade end (FIG. 9). The configuration and the angle of the handle connection may also vary (including but not limited to options on FIGS. 4A, 4B, 4C, and 4D). The shape of the handle may vary as well.

The end of the blade 14 may have a slightly upturned tip 16, and/or may include serrations 17 or otherwise rough surface to prevent the tissue or organ from slipping off the end of the blade.

Figure 11A:
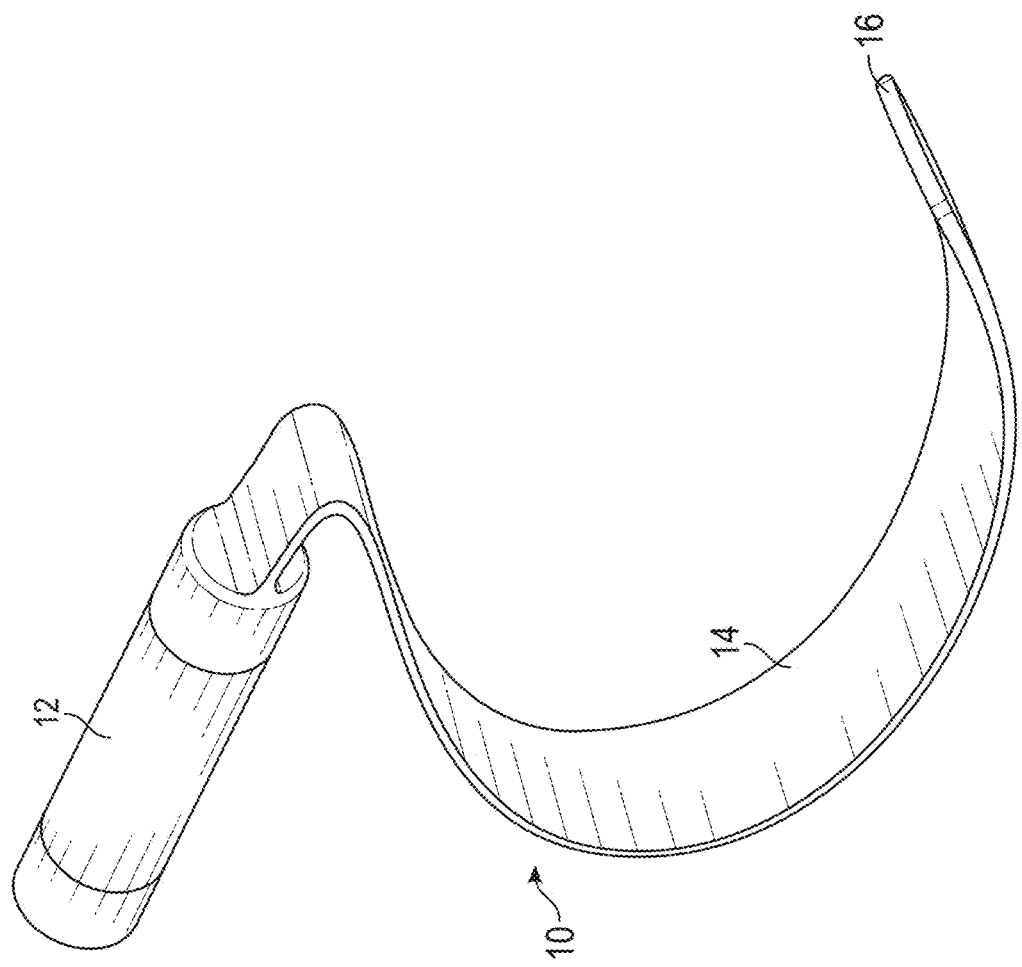
FIGS. 11A and 11B show a pair of retractors, one having a narrow blade and one having a wider blade.
Figure 11B:
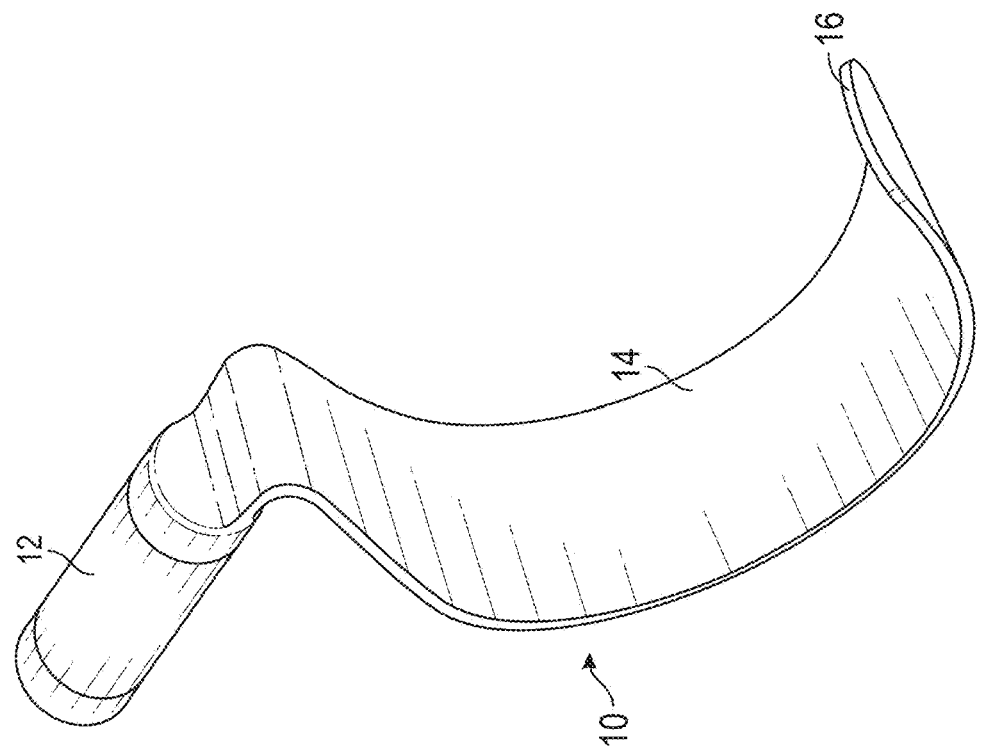
Figure 12:
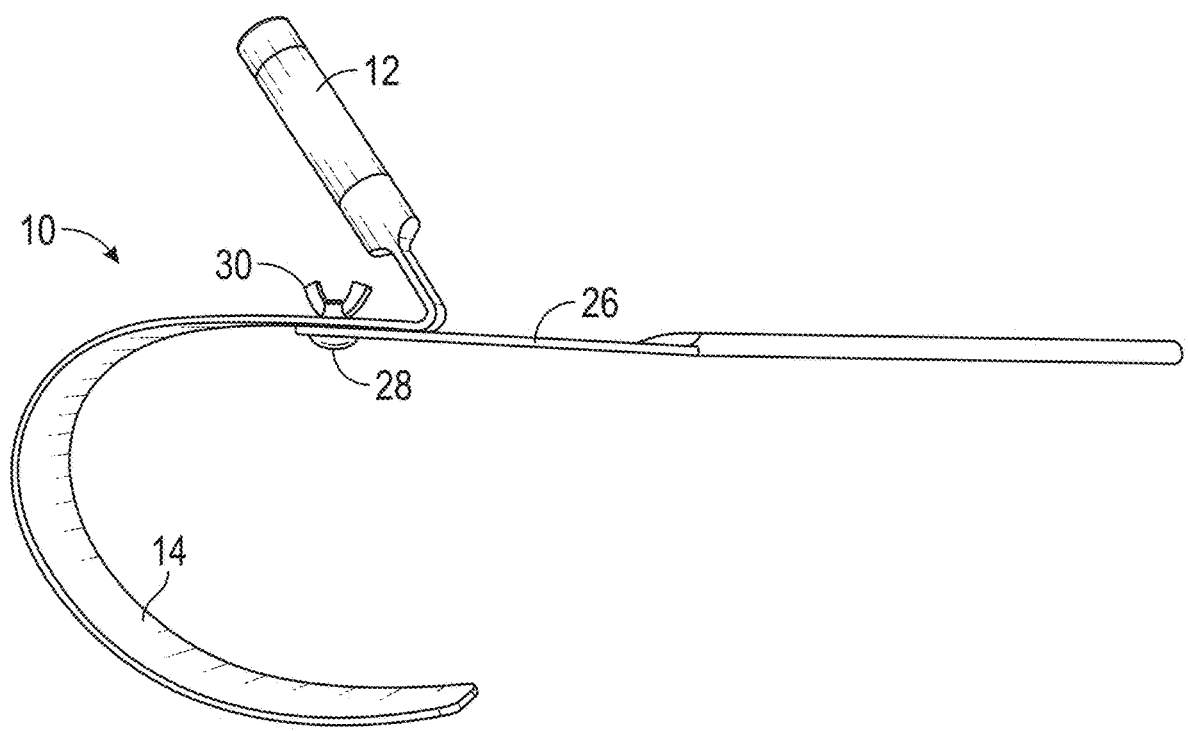
FIG. 12 is a perspective view of an embodiment of the transhiatal mediastinal retractor with an adapter mounted thereon.

In the preferred embodiments, the acute angle is approximately 45°, but may range from 10-80° (FIGS. 4A, 4B, 4C, and 4D). In the preferred embodiments, the blade 14, 14A has a flat cross section along its full length. However, the blade 14 may also be convex or concave for at least a portion of the blade beginning at the tip, as shown in FIGS. 7 and 8. The width of the blade 14 may vary, depending upon the patient (FIG. 11A and FIG. 11B). For example, a standard size blade is shown in comparison to a wider blade for patients with wider diaphragmatic hiatus.

The size of the blade opening ("depth of retractor") may also vary depending on the patient. In FIG. 9, a standard sized retractor is shown on top, as compared to the larger bariatric retractor (deeper and wider "C") on the bottom. FIG. 9 also shows in broken lines alternative lengths for the blade 14, as well as alternative angles of the blade tip 16.

Figure 13:
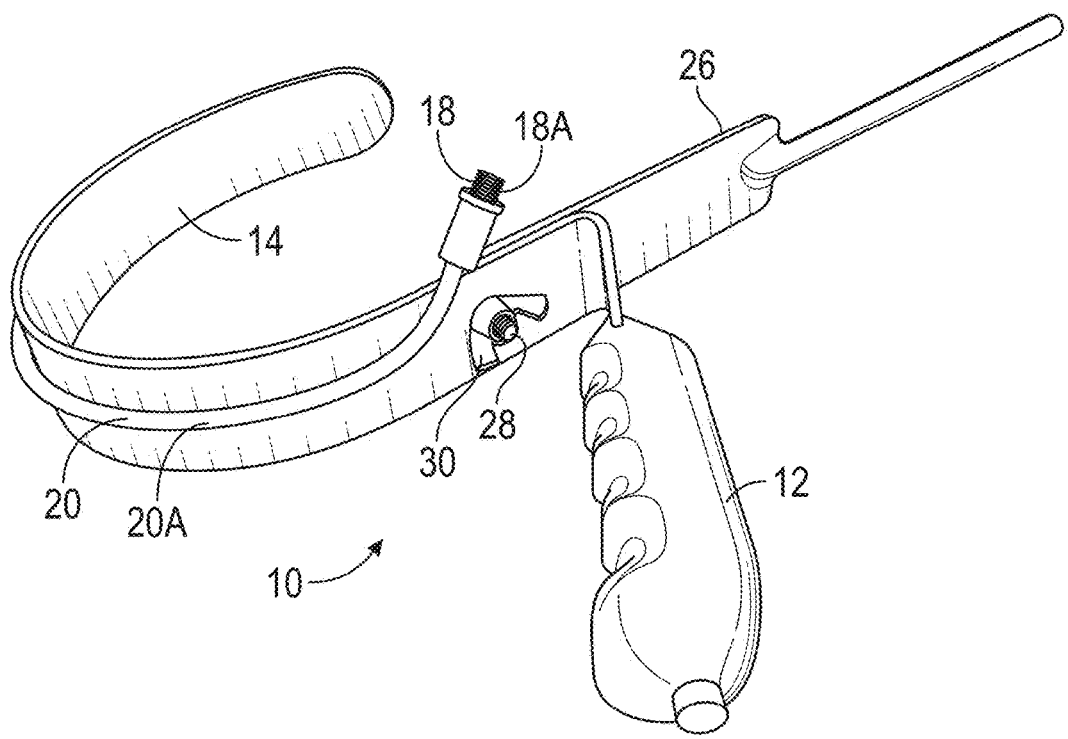
FIG. 13 is another perspective view of an embodiment of the transhiatal mediastinal retractor with a conduit useful for housing light sources and/or a camera, attached to an adapter for a table-mounted retractor system.
Figure 15:
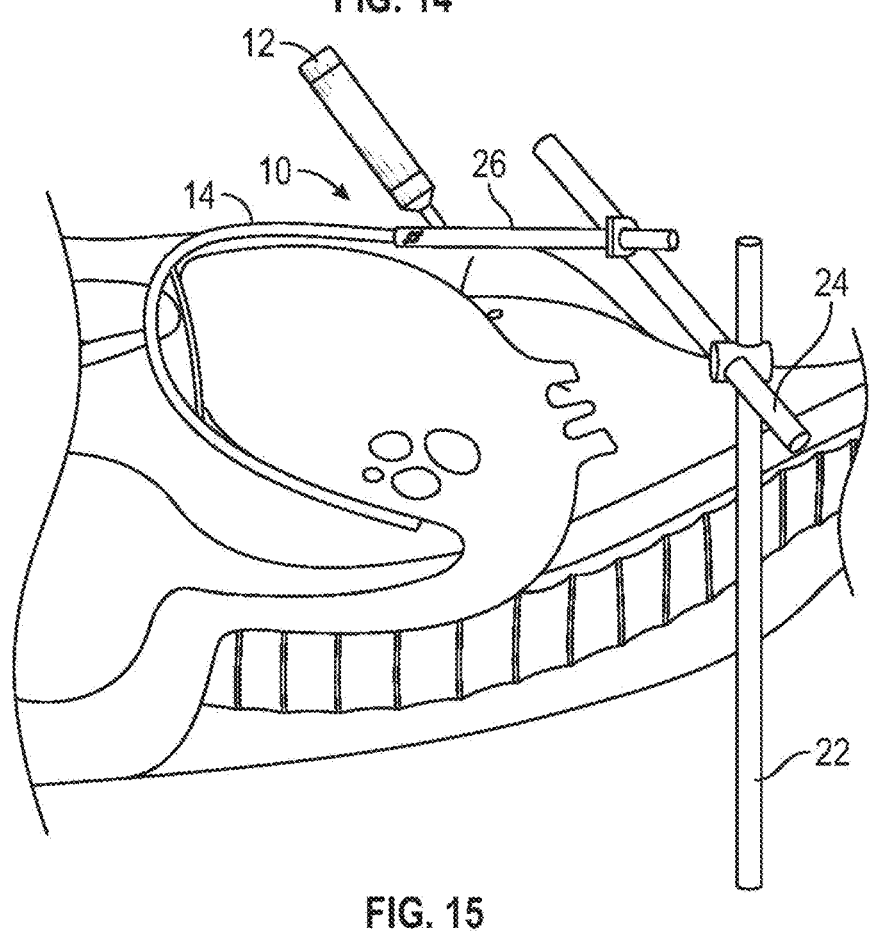
FIG. 15 is a view an embodiment of the table-mounted transhiatal mediastinal retractor engaged in the thoracic cavity and attached by the means of an adapter to a table-mounted retractor system.

In another alternative embodiment, a light 18 may be attached to the blade, as shown in FIGS. 13 and 15. The light may be powered by any convenient means, including an electrical connection to a power source, for example, a battery. The light 18 is preferably an LED, which may be connected to the power source by a wire 20 extending along the back of the blade 14. It is understood that other types of light may also be used on the retractor tool 10, such as a fiber optic light 18A with a fiber optic cable 20A secured to the back of the blade 14.

Figure 14:
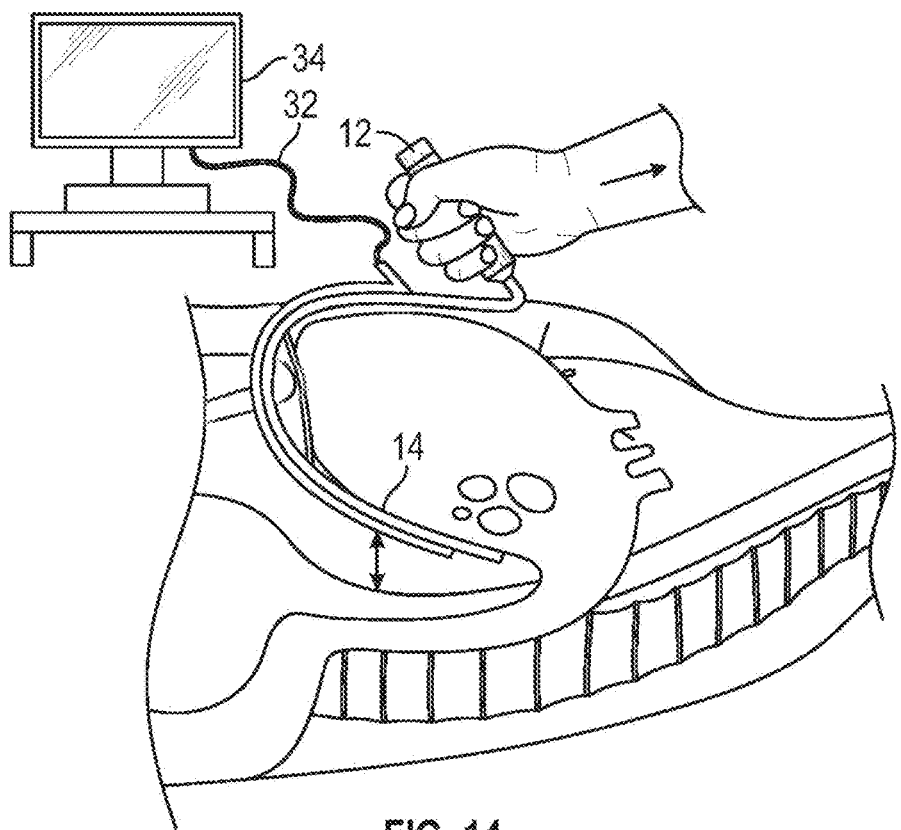
FIG. 14 is diagrammatic view of an embodiment of the light-and-video-mounted transhiatal mediastinal retractor engaged in the thoracic cavity.

The retractor tool 10 may also be used with a table mount system, as shown in FIG. 15. The table mount system includes one or more adjustable posts 22, 24 secured to a surgical table or bed by any convenient means, such as a clamp. The table mount system also includes an adapter 26 adjustably fixed to one of the posts 22, 24 and removably attached to the retractor 10, by any convenient means, such as a bolt 28 and wingnut 30 (FIG. 13) or quick release mechanism. The table mount system frees the surgeon or other medical personnel from holding the retractor tool 10 during the surgical procedure. In a further embodiment, the retractor 10 may include a camera (also designated by reference numeral 18 or 18A in FIG. 13) which is connected by hardwire 32 or wirelessly to a monitor 34 (FIG. 14). The camera allows the surgical team to visually inspect the thoracic cavity during surgery via the monitor 34.

The retractor 10 can be used for various operations on the diaphragmatic hiatus and the posterior mediastinum. In particular, the retractor instrument or tool of the present invention can be used in a transhiatal esophagostomy, in place of the conventional, multi-purpose abdominal Deaver retractor. The retractor 10 is preferably stiff and non-flexible to allow for precise control of the tissue and organ being moved during surgery. Also, the angle of retraction, preferably approximately 45°, for the non-bendable blade, improves the field of view of the posterior mediastinum for the surgeon. The non-bendable blade provides for a more stable retraction of the tissue and organs.

Thus, applicant's retractor instrument can be used by general thoracic and for gut surgeons performing open transhiatal esophagostomies and other operations in the diaphragmatic hiatus. The different width and depth of the blades can accommodate variations in patient anatomies.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A surgical tool for transhiatal mediastinal retraction, comprising:
    a handle;
    a blade extending forwardly from the handle and having an acute bend extending rearwardly and then curving forwardly and upwardly to an end defining an open mouth.

2. The surgical tool of claim 1, wherein the mouth is open in a forward direction.

3. The surgical tool of claim 1, wherein the blade is flat.

4. The surgical tool of claim 1, wherein the blade is concave in cross section.

5. The surgical tool of claim 1, wherein the blade is convex in cross section.

6. The surgical tool of claim 1, further comprising a light on the blade.

7. The surgical tool of claim 1, wherein the blade is substantially non-flexible.

8. The surgical tool of claim 1, wherein the acute bend is ranges from 10-80°.

9. The surgical tool of claim 8, wherein the bend is approximately 45°.

10. The surgical tool of claim 1, further comprising of a camera.

11. A surgical tool for transhiatal mediastinal retraction, comprising:
 a handle;
 a blade extending forwardly from the handle and having an acute bend extending rearwardly and then curving forwardly and upwardly to an end defining an open mouth;
 a table mount system attachable to the blade-to mount the blade to a table.

12. The surgical tool of claim 11, wherein the table mount system includes a fastener.

13. The surgical tool of claim 12, wherein the fastener is selected from a wing nut, a notch, a bolt, and a quick release fitting.

14. The surgical tool of claim 11, wherein the table mount system includes an adapter.

15. The surgical tool of claim 14, wherein the adapter is selected from of a rod, a bar, and a paddle.

16. The surgical tool of claim 11, wherein the table mount system includes a securing arm.

17. The surgical tool of claim 16, wherein the securing arm comprises a pole with clamp.

18. The surgical tool of claim 11, further comprises a camera.

19. A surgical tool for illuminating the thoracic cavity, comprising:
 a handle;
 a blade extending forwardly from the handle and having an acute bend extending rearwardly and then curving forwardly and upwardly to an end defining an open mouth,
 a light source on the blade; and
 a power source electrically connected to the light source.

20. The surgical tool of claim 19, wherein the power source is electrically connected to the light source at a location remote from the retractor, and the light source emits light though a fiber optic cable, and wherein the fiber optic cable is positioned along the exterior side of the blade.

21. The surgical tool of claim 19, wherein the light source is an LED and the electrical connection is a wire connected to the LED.

22. The surgical tool of claim 21, wherein the wire is flexibly connected to the power source.

23. The surgical tool of claim 21, further comprising a conduit positioned along an exterior side of the blade through which the wire extends.

24. The surgical tool of claim 19, further comprising a camera on the blade and electrically connected to the power source.

25. The surgical tool of claim 24, wherein the camera is operatively connected to a monitor allowing for the visualization of the thoracic cavity.

* * * * *